United States Patent
Terrell

[11] Patent Number: 5,969,193
[45] Date of Patent: Oct. 19, 1999

[54] METHOD FOR THE PREPARATION OF SEVOFLURANE

[75] Inventor: Ross C. Terrell, Phillipsburg, N.J.

[73] Assignee: Medeva Pharmaceuticals PA, Inc., Bethlehem, Pa.

[21] Appl. No.: 08/912,520

[22] Filed: Aug. 18, 1997

[51] Int. Cl.$^6$ .................................................... C07L 41/00
[52] U.S. Cl. ........................................................... 568/683
[58] Field of Search ............................................. 568/683

[56] References Cited

U.S. PATENT DOCUMENTS

| | | |
|---|---|---|
| 3,683,092 | 8/1972 | Regan et al. . |
| 3,897,502 | 7/1975 | Russell et al. . |
| 3,911,024 | 10/1975 | Croix . |
| 4,250,334 | 2/1981 | Coon et al. . |
| 4,328,376 | 5/1982 | Berger et al. . |
| 4,874,901 | 10/1989 | Halpern et al. . |
| 4,874,902 | 10/1989 | Huang et al. . |
| 4,996,371 | 2/1991 | Halpern et al. . |
| 5,886,239 | 3/1999 | Kudzma ................................. 568/684 |

FOREIGN PATENT DOCUMENTS

| | | |
|---|---|---|
| 0 482 938 B1 | 4/1992 | European Pat. Off. . |
| 28 23 969 A1 | 12/1979 | Germany . |

OTHER PUBLICATIONS

Halpern, "Recent Developments in Fluorine Substituted Volatile Anesthetics", OrganoFluorine Compounds in Medicinal Chemistry and Biomedical Applications, Ed. Filler, et al., Elsevier Science Publishers BV, 1993, pp. 101–133, 1993.

Yoneda "The Combination of Hydrogen Fluoride with Organic Bases as Fluorination Agents" Tetrahedron, No. 294, vol. 47, No. 29, pp. 5329–5365, 1991.

*Primary Examiner*—Michael L. Shippen
*Attorney, Agent, or Firm*—Popovich & Wiles, P.A.

[57] ABSTRACT

A method for the preparation of sevoflurane which comprises (a) providing a liquid mixture of $(CF_3)_2CHOCH_2Cl$, hydrogen fluoride, and an amine and (b) reacting the mixture, to form $(CF_3)_2CHOCH_2F$.

25 Claims, No Drawings

METHOD FOR THE PREPARATION OF SEVOFLURANE

FIELD OF THE INVENTION

The present invention relates to the field of inhalation anesthetics. In particular, the present invention relates to a method for the preparation of sevoflurane.

BACKGROUND OF THE INVENTION

The development of fluorine substituted volatile anesthetics has revolutionized surgery. The fluorine substituted volatile anesthetics which are now available have properties which approach ideal drug behavior. In use, the fluorinated volatile anesthetics are inhaled by a patient, dissolve in the patient's blood and rapidly produce unconsciousness. Unconsciousness is maintained while administration is continued, and upon discontinuing administration they are exhaled. As the anesthetics are exhaled, the patient returns to consciousness. An ideal fluorine containing volatile anesthetic produces quality anesthesia, has rapid onset, rapid recovery, muscle relaxation, sedation, and analgesia.

Commercially available volatile fluorinated anesthetics include desflurane ($CF_3CHFOCHF_2$), enflurane ($CHClFCF_2OCHF_2$), halothane ($CF_3CHBrCl$), isoflurane ($CF_3CHClOCHF_2$) and sevoflurane (($CF_3$)$_2CHOCH_2F$). The physical properties of volatile fluorinated anesthetics are important to the anesthesiologist. These physical properties include boiling point, specific gravity, vapor density, vapor pressure, oil/gas partition coefficient and blood/gas partition coefficient (percent of the anesthetic found in a known quantity of blood versus the percent found in a known volume of atmosphere above the blood sample). The blood-gas partition coefficient is considered to be particularly important, as it serves as a significant aid in predicting the time a patient needs to awaken from anesthesia.

Although each of the molecules depicted above has its own unique characteristics that provide a set of parameters needed to commercially develop it as an anesthetic, the chemical properties and chemical purity of the fluorinated volatile anesthetic are particularly important. Of particular interest is the general reactivity of the compound, as well as the stability of the anesthetic to light, air, soda-lime, and a variety of metals and nonmetallic materials which may contact the anesthetic during a normal surgical procedure. Additionally, the minimum flammable concentration of the anesthetic in pure oxygen, or 70% nitrous oxide and 30% oxygen, must be determined to ensure that it is well out of the range of the effective concentration of anesthetic used in surgery.

The chemical purity of the fluorine substituted volatile anesthetic is of utmost importance, requiring clean methods of production and extensive manufacturing controls. Additionally, the synthesis of these anesthetics requires consideration of many factors not normally encountered in the medicinal chemistry arena, i.e., the need to produce millions of pounds of pharmaceuticals with the highest standards of purity. In contrast to volatile anesthetics, many drugs are typically administered in milligram quantities. As a result, a fraction of a percent of an impurity in a few milligrams of a drug can be easily eliminated by the patient. However, since 10 to 50 grams of a volatile anesthetic are typically used during the course of a normal surgical procedure, the same concentration of impurity can reach a toxic level. Accordingly, it is highly desirable to find synthetic routes that give high purity fluorine substituted volatile anesthetics.

The compound 1,1, 1,3,3,3-hexafluoroisopropyl fluoromethyl ether (also known as sevoflurane) is an important volatile anesthetic agent particularly suited for administration to patients during outpatient surgery. Sevoflurane is known to provide patients with a rapid rate of recovery from the anesthesia. An additional advantage of this anesthetic agent is that it can be used as an induction agent since it is not pungent and allows a rapid and smooth induction without breath holding or laryngospasm as may occur with other inhalation agents. A smooth uneventful induction is especially valuable for pediatric anesthesia where the use of intravenous induction agents can result in numerous problems and is often contraindicated.

A number of methods of preparing 1,1, 1,3,3,3-hexafluoroisopropyl fluoromethyl ether have been described. U.S. Pat. No. 3,683,092 describes four methods of preparation, three of which start with 1,1,1,3,3,3-hexafluoroisopropyl methyl ether. This ether is a well known compound, the preparation of which is described in U.S. Pat. No. 3,911,024. The specific reaction chemistries disclosed in the '092 patent are summarized below:

$$(CF_3)_2CHOCH_3+Cl_2\rightarrow(CF_3)_2CHOCH_2Cl\rightarrow(CF_3)_2CHOCH_2F \quad (1)$$

In equation (1), the chlorinated ether is converted to the fluorinated form by reacting it in the presence of potassium fluoride (KF) in sulfolane.

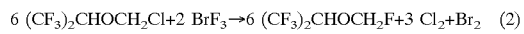

$$6\ (CF_3)_2CHOCH_2Cl+2\ BrF_3\rightarrow 6\ (CF_3)_2CHOCH_2F+3\ Cl_2+Br_2 \quad (2)$$

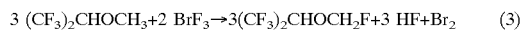

$$3\ (CF_3)_2CHOCH_3+2\ BrF_3\rightarrow 3(CF_3)_2CHOCH_2F+3\ HF+Br_2 \quad (3)$$

None of the three routes above are suitable for economical large scale manufacture. The method employing potassium fluoride requires high temperatures and long reaction times. The other two methods require the use of expensive and dangerous bromine trifluoride.

The fourth method described in the '092 patent starts with 1,1,1,3,3,3-hexafluoroisopropanol which is reacted with hydrogen fluoride and formaldehyde in a fluoromethylation reaction as shown in reaction (4):

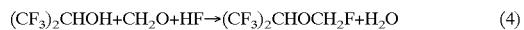

$$(CF_3)_2CHOH+CH_2O+HF\rightarrow(CF_3)_2CHOCH_2F+H_2O \quad (4)$$

Although reaction (4) uses economical reagents and is potentially attractive in a commercial synthesis, yields are poor due to the formation of polyether byproducts.

Several other methods for preparation of 1,1,1,3,3,3-hexafluoroisopropyl fluoromethyl ether have also been reported. For example, a direct fluorination reaction using elemental fluorine in argon was reported in U.S. Pat. No. 3,897,502. The reaction is shown in equation (5) below:

$$(CF_3)_2CHOCH_3\rightarrow(CF_3)_2CHOCH_2F \quad (5)$$

The reaction of equation (5) is carried out in the presence of fluorine ($F_2$) and argon. The method of the '502 patent is not suitable for large scale commercial synthesis since yields are not good and the method uses elemental fluorine, an expensive and difficult to handle reagent.

U.S. Pat. No. 4,874,901 discloses a halogen exchange reaction using NaF under supercritical conditions (temperature: 250–325° C., pressure: 60 to 80 atmospheres) as described in reaction (6) below:

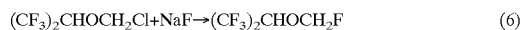

$$(CF_3)_2CHOCH_2Cl+NaF\rightarrow(CF_3)_2CHOCH_2F \quad (6)$$

The utility of the method of the '901 patent is limited because of the extremely high temperatures and pressures required.

A fluorodecarboxylation synthesis was reported in U.S. Pat. No. 4,996,371 as shown in equation (7):

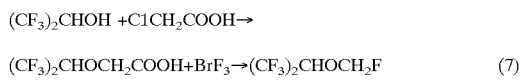

$$(CF_3)_2CHOH + ClCH_2COOH \rightarrow$$
$$(CF_3)_2CHOCH_2COOH + BrF_3 \rightarrow (CF_3)_2CHOCH_2F \quad (7)$$

Again, the method of the '371 patent uses the expensive and dangerous bromine trifluoride reactant and is not suitable for commercial manufacture.

Another even more expensive synthesis using large quantities of bromine trifluoride is described in U.S. Pat. No. 4,874,902. The reaction chemistry of the '902 patent is exemplified below:

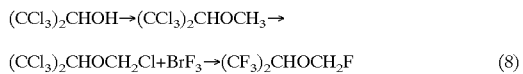

$$(CCl_3)_2CHOH \rightarrow (CCl_3)_2CHOCH_3 \rightarrow$$
$$(CCl_3)_2CHOCH_2Cl + BrF_3 \rightarrow (CF_3)_2CHOCH_2F \quad (8)$$

A further method of synthesis claimed to be suitable for manufacture of 1,1,1,3,3,3 hexafluoroisopropyl fluoromethyl ether on a large scale is described in U.S. Pat. No. 4,250,334; this method starts with hexafluoroisopropanol and uses hydrogen fluoride and sulfuric acid as reactants as shown in equation (9):

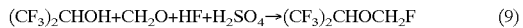

$$(CF_3)_2CHOH + CH_2O + HF + H_2SO_4 \rightarrow (CF_3)_2CHOCH_2F \quad (9)$$

Although yields of 90% are claimed, conversions are only 33 to 38%. The method of the '334 patent suffers the further disadvantage that a large stoichiometric excesses of formaldehyde, hydrogen fluoride, and sulfuric acid are required. The use of such excesses could result in large amounts of hazardous waste byproducts containing formaldehyde, a known carcinogen. It is also possible that this waste product would contain bis-fluoromethyl ether, structurally related to the carcinogenic bis-chloromethyl ether.

Synthesis of fluoroethers has been reported in DE 2823969 A1. As taught in that publication, a number of chloromethyl ethyl and chloromethyl n-propyl ethers were reacted with amines and anhydrous hydrogen fluoride to give the corresponding fluoromethyl ethers. Example 1 of the '969 publication is given in equation (10):

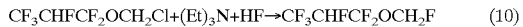

$$CF_3CHFCF_2OCH_2Cl + (Et)_3N + HF \rightarrow CF_3CHFCF_2OCH_2F \quad (10)$$

However, the reaction of the more sterically hindered and predictably less reactive isopropyl chloromethylethers was not reported.

It would therefore be desirable to have a synthesis of 1,1,1,3,3,3-hexafluoroisopropyl fluoromethyl ether which does not use expensive reagents, such as elemental fluorine or bromine trifluoride, does not involve the use of high temperatures and pressures, and does not create large amounts of hazardous waste as a byproduct.

SUMMARY OF THE INVENTION

The invention provides a method for the preparation of sevoflurane which comprises (a) providing a liquid mixture of $(CF_3)_2CHOCH_2Cl$, hydrogen fluoride, and an amine and (b) reacting the mixture, to form $(CF_3)_2CHOCH_2F$.

The invention also provides a method for the preparation of sevoflurane which comprises: (a) providing $(CF_3)_2CHOCH_3$; (b) contacting the $(CF_3)_2CHOCH_3$ with chlorine gas; (c) exposing the mixture to a sufficient amount of light to initiate and sustain an exothermic reaction; (d) allowing the exothermic reaction to proceed to produce a $(CF_3)_2CHOCH_2Cl$ intermediate; and (e) reacting in a liquid mixture the $(CF_3)_2CHOCH_2Cl$ intermediate with hydrogen fluoride and an amine, to form $(CF_3)_2CHOCH_2F$.

Additional features and advantages of the invention are set forth in the description which follows and in part will be apparent from the description. The objectives and other advantages of the invention will be realized and attained by the method of preparation of sevoflurane as particularly pointed out in the written description and claims.

It is to be understood that both the foregoing general description and the following detailed description are exemplary and explanatory and are intended to provide furter explanation of the invention as claimed.

DESCRIPTION OF THE PREFERRED EMBODIMENT

The invention provides a method for the preparation of sevoflurane which comprises (a) providing a liquid mixture of $(CF_3)_2CHOCH_2Cl$, hydrogen fluoride, and an amine and (b) reacting the mixture, to form $(CF_3)_2CHOCH_2F$. In a preferred embodiment the mixture is reacted by heating, preferably at 40° C. to 80° C. or at 55° C. to 65° C. Typically, the reaction is conducted by heating the mixture for a period of four to twelve hours, preferably four to ten hours and more preferably four to seven hours.

The amine preferably is selected from a primary amine, a secondary amine, or a tertiary amine. The amine can be propylamine or diethylamine. The amine preferably is a tertiary amine, more preferably, a trialkylamine. In preferred embodiments, the trialkylamine is selected from triethylamine, tripropylamine, triisopropylamine, tributylamine, dimethyl ethyl amine, di-isopropyl ethyl amine or mixtures thereof. The amine can also be a cyclic amine. The cyclic amine preferably is selected from pyrrolidine, N-methyl pyrrolidine, or piperidine.

The mixture can comprise $(CF_3)_2CHOCHCl_2$. If $(CF_3)_2CHOCHCl_2$ is present, the mixture preferably can comprise from 0.01 to 20 percent by weight of $(CF_3)_2CHOCHCl_2$.

The mixture can comprise water. Preferably, the mixture can comprise 1 to 25 percent by weight of water, 1 to 15 percent by weight of water, or 3 to 10 percent by weight of water.

The reaction stoichiometry typically requires one mole of hydrogen fluoride per mole of $(CF_3)_2CHOCH_2Cl$, however an excess of HF can also be used. The mole ratio of the $(CF_3)_2CHOCH_2Cl$ to the hydrogen fluoride in the mixture preferably is from 1:1 to 1:2. Although the amount of amine used is not critical, the mole ratio of the $(CF_3)_2CHOCH_2Cl$ to the amine in the mixture preferably is from 1:0.3 to 1:2. In a preferred embodiment, the mole ratio of the $(CF_3)_2CHOCH_2Cl$ to the amine to the hydrogen fluoride is in the range of :1:11 to 1:2:2.

The yield of the reaction is preferably greater than 50 percent, more preferably greater than 65 percent, and more preferably greater than 75 percent. The conversion of the reaction is preferably greater than 50 percent, more preferably greater than 60 percent, and more preferably greater than 70 percent.

In a preferred embodiment, the $(CF_3)_2CHOCH_2F$ can be separated from the mixture after the mixture has reacted by washing the mixture with water. In other embodiments the $(CF_3)_2CHOCH_2F$ can be separated from the mixture by steam distillation or by fractional distillation. In another embodiment, the $(CF_3)_2CHOCH_2F$ can be separated from the mixture by distillation with an inert high boiling solvent having a boiling point above that of sevoflurane. In one embodiment, the high boiling solvent is an aromatic hydrocarbon, preferably xylene. The distillation with the inert high boiling solvent can proceed simultaneously with reacting the mixture.

The invention provides a method for the preparation of sevoflurane which comprises: (a) providing $(CF_3)_2CHOCH_3$; (b) contacting the $(CF_3)_2CHOCH_3$ with chlorine gas; (c) exposing the mixture to a sufficient amount of light to initiate and sustain an exothermic reaction; (d) allowing the exothermic reaction to proceed to produce a $(CF_3)_2CHOCH_2Cl$ intermediate; and (e) reacting in a liquid mixture the $(CF_3)_2CHOCH_2Cl$ intermediate with hydrogen fluoride and an amine, to form $(CF_3)_2CHOCH_2F$. The light is preferably ultraviolet light. All the preferred parameters for step (e) are similar to those described elsewhere in this specification.

Because isolation of the $(CF_3)_2CHOCH_2Cl$ intermediate is not necessary, the $(CF_3)_2CHOCH_3$ can be photochemnically chlorinated and then immediately reacted with the hydrogen fluoride and the amine. Thus, the present invention is useful for a one pot synthesis.

Photochlorination can be achieved by adding the required amount of chlorine to $(CF_3)_2CHOCH_3$ while illuminating the mixture with light, preferably ultraviolet light. The photochlorinated mixture can be reacted with hydrogen fluoride and an amine without further purification to produce $(CF_3)_2CHOCH_2F$.

The HF-amine complex is typically prepared in advance by reacting either anhydrous HF or a concentrated aqueous solution of HF with an amine such as a primary, secondary or tertiary amine.

In addition to those listed above, some of the amines that can be sed for making the HF complexes are of the general formula:

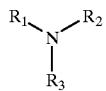

wherein $R_1$ is a $C_1$–$C_{12}$ primary, secondary, or tertiary alkyl group and $R_2$ and $R_3$ are, independently, hydrogen or $C_1$–$C_{12}$ primary, secondary or tertiary alkyl groups. Useful amines include, but are not limited to, methylamine, dimethylamine, trimethylamine, ethylamine, diethylamine, triethylamine, propylamine, dipropylamine, tripropylamine, isopropylamine, diisopropyl amine, triisopropyl amine, diethyl methyl amine, di-isopropyl ethyl amine, n-butyl amine, n-dibutyl amine, n-tributyl amine, s-butyl amine, s-dibutyl amine, t-butyl amine, tripentylamine, trihexylamine, triheptylamine, and trioctylamine.

The amine can also be a cyclic amine such as pyrrolidine, N-methyl pyrrolidine, or piperidine.

A further advantage of this invention is that it allows both the monochloro- and dichlo- ethers to be present during the reaction. Thus, the monochloroether $(CF_3)_2CHOCH_2Cl$ can be reacted while in the presence of the dichloroether $(CF_3)_2CHOCHCl_2$. The dichloroether $(CF_3)_2CHOCHCl_2$ preferably does not make up more than 20 percent by weight of the reaction mixture. It is surprising that the monochloro- and dichlo- ethers can be mixed and the reaction performed under the conditions employed. As a result, it is not necessary to separate mixtures of monochloro- and dichlo- ethers prior to carrying out the fluorination reaction.

The dichloroether is formed during the synthesis of the monochloroether. In the present invention, the dichloroether and the monochloroether can be used together in the fluorination reaction because the dichloroether does not react under the conditions employed. Thus, the present method eliminates a distillation step to remove the dichloroether, thereby making the overall reaction simpler and more efficient.

EXAMPLES

Example 1

An aqueous 48% HF solution (20.8 g, 0.5 mole of HF) was added to diethyl methyl amine (43.5 g, 0.5 mole) with cooling. $(CF_3)_2CHOCH_2Cl$ (108 g, 0.5 mole) was then added and the reaction mixture heated at 50–60° C. for 5 hrs. At the end of this time, the product was isolated by washing with water to recover 82 g. This product was analyzed by gas chromatography using a 15x⅛" 20% carbowax on chromosorb column at 125° C. The product had the following composition: $(CF_3)_2CHOCH_2F$, 51%, $(CF_3)_2CHOCH_2Cl$, 42%, and $(CF_3)_2CHOH$, 5.4%. This represents a conversion of 41% and a yield of 60%.

Example 2

An aqueous 48% HF solution (20.8 g, 0.5 mole of HF) was added to dimethyl ethyl amine (36.5 g, 0.5 mole) with cooling. $(CF_3)_2CHOCH_2Cl$ (108 g, 0.5 mole) was then added and the reaction mixture heated at 50–60° C. for 5 hrs. At the end of this time, the product was isolated by washing with water to recover 65 g. This product was analyzed by gas chromatography using a 15'x⅛" 20% carbowax on chromosorb column at 125° C. The product had the following composition: $(CF_3)_2CHOCH_2F$, 34%, $(CF_3)_2CHOCH_2Cl$, 63%, and $(CF_3)_2CHOH$, 2.6%. This represents a conversion of 22% and a yield of 35%.

Example 3

An aqueous 48% HF solution (20.8 g, 0.5 mole of HF) was added to N-methyl pyrrolidine (42.5 g, 0.5 mole) with cooling. $(CF_3)_2CHOCH_2Cl$ (108 g, 0.5 mole) was then added and the reaction mixture heated at 50–60° C. for 6 hrs. At the end of this time, the product was isolated by washing with water to recover 51 g. This product was analyzed by gas chromatography using a 15'x⅛" 20% carbowax on chromosorb column at 125° C. The product had the following composition: $(CF_3)_2CHOCH_2F$, 45%, $(CF_3)_2CHOCH_2Cl$, 53%, and $(CF_3)_2CHOH$, 1.5%. This represents a conversion of 22% and a yield of 45%.

Example 4

An aqueous 48% HF solution (31.2 g, 0.75 mole) and 30cc of water was added to triethyl amine (75 g, 0.75 mole) with cooling. $(CF_3)_2CHOCH_2Cl$ (108 g, 0.5 mole) was then added and the reaction mixture heated at 50° C. for 16 hrs. At the end of this time, the product was isolated by azeotropic distillation from water to recover 75 g. This product was analyzed by gas chromatography using a 15'x⅛" 20% carbowax on chromosorb column at 125° C. The product had the following composition: $(CF_3)_2CHOCH_2F$, 80%, $(CF_3)_2CHOCH_2C1$, 18%, and $(CF_3)_2CHOH$, 1.5%. This represents a conversion of 60% and a yield of 68%.

Example 5

An aqueous 48% HF solution (20.8 g, 0.5 mole of HF) was added to tripropyl amine (71.5 g, 0.5 mole) with cooling. $(CF_3)_2CHOCH_2Cl$ (108 g, 0.5 mole) was then added and the reaction mixture heated at 50–60° C. for 5 hrs. At the end of this time, the product was isolated by washing with water to recover 90 g. This product was analyzed by gas chromatography using a 15'×⅛" 20% carbowax on chromosorb column at 125° C. The product had the following composition: $(CF_3)_2CHOCH_2F$, 37%, $(CF_3)_2CHOCH_2Cl$, 57%, and $(CF_3)_2CHOH$, 5%. This represents a conversion of 33% and a yield of 62%.

Example 6

An aqueous 48% HF solution (20.8 g, 0.5 mole of HF) was added to tributyl amine (92.5 g, 0.5 mole) with cooling. $(CF_3)_2CHOCH_2Cl$ (108 g, 0.5 mole) was then added and the reaction mixture heated at 50–60° C. for 5 hrs. At the end of this time, the product was isolated by washing with water to recover 95 g. This product was analyzed by gas chromatography using a 15'×⅛" 20% carbowax on chromosorb column at 125° C. The product had the following composition: $(CF_3)_2CHOCH_2F$, 25%, $(CF_3)_2CHOCH_2Cl$, 69%, and $(CF_3)_2CHOH$, 5%. This represents a conversion of 24% and a yield of 60%.

Example 7

An aqueous 48% HF solution (21 g, 0.5 mole) was added to propylamine (29.5 g, 0.5 mole) with cooling. $(CF_3)_2CHOCH_2Cl$ (108 g, 0.5 mole) was then added and the reaction mixture heated at 60–65° C. for 6 hrs. At the end of this time, the product was isolated by washing with water to recover 88 g. This product was analyzed by gas chromatography using a 15'×⅛" 20% carbowax on chromosorb column at 125° C. The product had the following composition: $(CF_3)_2CHOCH_2F$, 13%, $(CF_3)_2CHOCH_2Cl$, 86%, and $(CF_3)_2CHOH$, 1%. This represents a conversion of 11% and a yield of 50%.

Example 8

An aqueous 48% HF solution (21 g, 0.5 mole) was added to diethyl amine (36 g, 0.5 mole) with cooling. $(CF_3)_2CHOCH_2Cl$ (108 g, 0.5 mole) was then added and the reaction mixture heated at 60–65° C. for 6 hrs. At the end of this time, the product was isolated by washing with water to recover 91 g. This product was analyzed by gas chromatography using a 15'×⅛" 20% carbowax on chromosorb column at 125° C. The product had the following composition: $(CF_3)_2CHOCH_2F$, 29%, $(CF_3)_2CHOCH_2Cl$, 69%, and $(CF_3)_2CHOH$, 1.7%. This represents a conversion of 25% and a yield of 65%.

Example 9

An aqueous 48% HF solution (21 g, 0.5 mole) was added to piperidine (42.5 g, 0.5 mole) with cooling. $(CF_3)_2CHOCH_2Cl$ (108 g, 0.5 mole) was then added and the reaction mixture heated at 60–65° C. for 5 hrs. At the end of this time, the product was isolated by washing with water to recover 88 g. This product was analyzed by gas chromatography using a 15'×⅛" 20% carbowax on chromosorb column at 125° C. The product had the following composition: $(CF_3)_2CHOCH_2F$, 37% $(CF_3)_2CHOCH_2Cl$, 54% and $(CF_3)_2CHOH$, 9%. This represents a conversion of 32% and a yield of 57%.

Example 10

An aqueous 48% HF solution (43.4 g, 1 mole) was added to triethyl amine (101 g, 1 mole) with cooling. $(CF_3)_2CHOCH_2Cl$ (108 g, 0.5 mole) was then added and the reaction mixture heated at 60–65° C. for 8 hrs. At the end of this time, the product was isolated by washing with water to recover 79 g. This product was analyzed by gas chromatography using a 15'×⅛" 20% carbowax on chromosorb column at 125° C. The product had the following composition: $(CF_3)_2CHOCH_2F$, 86%, $(CF_3)_2CHOCH_2Cl$, 3%, and $(CF_3)_2CHOH$, 11%. This represents a conversion of 67% and a yield of 68%.

Example 11

An aqueous 48% HF solution (21 g, 0.5 mole) was added to di-isopropyl ethyl amine (64.6 g, 0.5 mole) with cooling. $(CF_3)_2CHOCH_2Cl$ (108 g, 0.5 mole) was then added and the reaction mixture heated at 50–60° C. for 6 hrs. At the end of this time, the product was isolated by washing with water to recover 89 g. This product was analyzed by gas chromatography using a 15'×⅛" 20% carbowax on chromosorb column at 125° C. The product had the following composition: $(CF_3)_2CHOCH_2F$, 54%, $(CF_3)_2CHOCH_2Cl$, 37%, and $(CF_3)_2CHOH$, 8.6%. This represents a conversion of 47% and a yield of 65%.

Example 12

An aqueous 48% HF solution (21 g, 0.5 mole) was added to triethylamine (50 g, 0.5 mole) with cooling. $(CF_3)_2CHOCH_2Cl$ (108 g, 0.5 mole) was then added and the reaction mixture heated at 60–65° C. for 6 hrs. At the end of this time, the product was isolated by washing with water to recover 85 g. This product was analyzed by gas chromatography using a 15'×1/8" 20% carbowax on chromosorb column at 125° C. The product had the following composition: $(CF_3)_2CHOCH_2F$, 58%, $(CF_3)_2CHOCH_2Cl$, 35%, and $(CF_3)_2CHOH$, 6.6%. This represents a conversion of 48% and a yield of 73%.

Example 13

An aqueous 48% HF solution (20.8 g, 0.5 mole) was added to triethylamine (50 g, 0.5 mole) with cooling. $(CF_3)_2CHOCH_2Cl$ (54 g, 0.25 mole) was then added and the reaction mixture heated at 60–65° C. for 6 hrs. At the end of this time, the product was isolated by washing with water to recover 38 g. This product was analyzed by gas chromatography using a 15'×⅛ 20% carbowax on chromosorb column at 125° C. The product had the following composition: $(CF_3)_2CHOCH_2F$, 86%, $(CF_3)_2CHOCH_2Cl$, 0.5%, and $(CF_3)_2CHOH$, 13%. This represents a conversion of 65% and a yield of 65%.

Example 14

An aqueous 48% HF solution (14.6 g, 0.37 mole) was added to tertiary butyl amine (27 g, 0.37 mole) with cooling. $(CF_3)_2CHOCH_2Cl$ (54 g, 0.25 mole) was then added and the reaction mixture heated at 60–65° C. for 10 hrs. At the end of this time, the product was isolated by washing with water to recover 41 g. This product was analyzed by gas chromatography using a 15'×1/8" 20% carbowax on chromosorb column at 125° C. The product had the following composition: $(CF_3)_2CHOCH_2F$, 41%, $(CF_3)_2CHOCH_2Cl$, 55%, and $(CF_3)_2CHOH$, 4%. This represents a conversion of 34% and a yield of 57%.

Example 15

An aqueous 48% HF solution (14.6 g, 0.37 mole) was added to di-isopropyl ethyl amine (47 g, 0.37 mole) with cooling. $(CF_3)_2CHOCH_2Cl$ (54 g, 0.25 mole) was then added and the reaction mixture heated at 60–70° C. for 10 hrs. At the end of this time, the product was isolated by washing with water and dilute HCl to recover 43 g. This product was analyzed by gas chromatography using a 15'× 1/8" 20% carbowax on chromosorb column at 125° C. The product had the following composition: $(CF_3)_2CHOCH_2F$, 82%, $(CF_3)_2CHOCH_2Cl$, 0.8%, and $(CF_3)_2CHOH$, 16%. This represents a conversion of 70% and a yield of 70%.

Example 16

An aqueous 48% HF solution (14.6 g, 0.37 mole) was added to triethylamine (37 g, 0.37 mole) with cooling. $(CF_3)_2CHOCH_2Cl$ (54 g, 0.25 mole) was then added and the reaction mixture heated at 60–65° C. for 16 hrs. At the end of this time, the product was isolated by azeotropic distillation from water to recover 44 g. This product was analyzed by gas chromatography using a 15'×1/8" 20% carbowax on chromosorb column at 125° C. The product had the following composition: $(CF_3)_2CHOCH_2F$, 89%, $(CF_3)_2CHOCH_2Cl$, 0.14%, and $(CF_3)_2CHOH$, 9.9%. This represents a conversion of 78% and a yield of 78%.

Example 17

An aqueous 48% HF solution (19.8 g, 0.55 mole) was added to pyrrolidine (39 g, 0.55 mole) with cooling. $(CF_3)_2CHOCH_2Cl$ (108 g, 0.5 mole) was then added and the reaction mixture heated at 60–65° C. for 12 35 hrs. At the end of this time, the product was isolated by azeotropic distillation from water to recover 72 g. This product was analyzed by gas chromatography using a 15'×1/8" 20% carbowax on chromosorb column at 125° C. The product had the following composition: $(CF_3)_2CHOCH_2F$, 57%, $(CF_3)_2CHOCH_2Cl$, 34%, and $(CF_3)_2CHOH$, 8%. This represents a conversion of 41% and a yield of 54%.

Example 18

An aqueous 48% HF solution (19.8 g, 0.55 mole) was added to triethylamine (56 g, 0.55 mole) with cooling. $(CF_3)_2CHOCH_2Cl$ (108 g, 0.5 mole) was then added and the reaction mixare heated at 60° C. for 10 hrs. At the end of this time, the product was isolated by azeotropic distillation from water to recover 87 g. This product was analyzed by gas chromatography using a 15'×1/8 20% carbowax on chromosorb column at 125° C. The product had the following composition: $(CF_3)_2CHOCH_2F$, 68%, $(CF_3)_2CHOCH_2Cl$, 22%, and $(CF_3)_2CHOH$, 11%. This represents a conversion of 54% and a yield of 74%.

Example 19

A mixture of $(CF_3)_2CHOCH_2Cl$ (108 g, 0.5 mole), $(Et)_3N\cdot 3HF$ (29.7 g, 0.2 mole), $(Et)_3N$ (36.3 g, 0.36 mole), and 2 g of water was heated at 60° C. for six hours. The product (85 g) was isolated by washing the reaction mixture with water. This product was analyzed by gas chromatography using a 15'×1/8" 20% carbowax on chromosorb column at 125° C. The product had the following composition: 82% $(CF_3)_2CHOCH_2F$ and 18% $(CF_3)_2CHOCH_2Cl$. This represents a conversion of 69% and a yield of 80%.

Example 20

A mixture of $(CF_3)_2CHOCH_2Cl$ (108 g, 0.5 mole), $(Et)_3N\cdot 3HF$ (27 g, 0.17 mole), and $(Et)_3N$ (36.3 g, 0.36 mole) was heated at 60° C. for six hours. The product (80 g) was isolated by precipitation with water. This product was analyzed by gas chromatography using a 15'×1/8" 20% carbowax on chromosorb column at 125° C. The product had the following composition: 79% $(CF_3)_2CHOCH_2F$ and 21% $(CF_3)_2CHOCH_2Cl$. This represents a conversion of 66% and a yield of 75%.

Example 21

One hundred forty grams of a mixture containing $(CF_3)_2CHOCH_2Cl$ (77%) and $(CF_3)_2CHOCHCl_2$ (18%) was mixed with $(Et)_3N\cdot 3F$ (29.7 g) and $(Et)_3N$ (36.3 g) and heated at 60° C. for six hours. The product (113 g) was isolated by addition of water. This product was analyzed by gas chromatography using a 15'×1/8" 20% carbowax on chromosorb column at 125° C. The product had the following composition: 61% $(CF_3)_2CHOCH_2F$, 16% $(CF_3)_2CHOCH_2Cl$ and 15% $(CF_3)_2CHOCHCl_2$. This represents a conversion of 69% and a yield of 83%.

Example 22

$(CF_3)_2CHOCH_2Cl$ (432 g, 2 moles) was mixed with $(Et)_3N\cdot 3HF$ (128 g, 0.8 moles), $(Et)_3N$ (158 g, 1.6 moles), and 300 g of xylene. This mixture was heated to 80° C. and the product distilled out using a 3'×1" distillation column packed with 1/4" stainless steel protruded packing. 311 g was distilled out over a period of three hours, the pot temperature rising to 110° C. Water was then added and an additional 64 g distilled at 53–60 ° C. The two distillates were combined and washed with water and aqueous 5% HCl to give 350 g of product. This product was analyzed by gas chromatography using a 15'×1/8" 20% carbowax on chromosorb column at 125° C. The product had the following composition: 84% $(CF_3)_2CHOCH_2F$ and 14% $(CF_3)_2CHOCH_2Cl$. This represents a conversion of 73% and a yield of 82%.

Example 23

$(CF_3)_2CHOCH_2Cl$ (108 g, 0.5 mole) was mixed with $(Et)_3N\cdot 3HF$ (54 g, 0.34 mole) and $(Et)_3N$ (66 g, 0.66 mole) and heated at 60–70° C. for six hours. Water was added and the insoluble product (80.5 g) separated. This product was analyzed by gas chromatography using a 15'×1/8" 20% carbowax on chromosorb column at 125° C. The product had the following composition: 96% $(CF_3)_2CHOCH_2F$ and 4% $(CF_3)_2CHOCH_2Cl$. This represents a conversion of 78% and a yield of 80%.

Example 24

$(CF_3)_2CHOCH_2Cl$ (108 g, 0.5 mole) was mixed with $(Et)_3N\cdot 3BF$ (40 g, 0.25 mole) and $(Et)_3N$ (50 g, 0.5 mole) and heated at 60° C. with stirring for six hours. The product was diluted with water and the insoluble product (80 g) separated. This product was analyzed by gas chromatography using a 15'×1/8" 20% carbowax on chromosorb column at 125° C. The product had the following composition: 90% $(CF_3)_2CHOCH_2F$ and 10% $(CF_3)_2CHOCH_2Cl$. This represents a 72% conversion and 80% yield.

Example 24

$(CF_3)_2CHOCH_2Cl$ (108 g, 0.5 mole) was mixed with $(Et)_3N\cdot 3HF$ (29.7 g, 0.18 mole) and $(Et)_3N$ (36 g, 0.36 mole) and heated at 60° C. with stirring for eight hours. Water was added and the insoluble product (76 g) separated. This product was analyzed by gas chromatography using a 15'×1/8" 20% carbowax on chromosorb column at 125° C. The product had the following composition: 91% $(CF_3)_2CHOCH_2F$ and 9% $(CF_3)_2CHOCH_2Cl$. This represents a 69% conversion and 77% yield.

Example 26

$(CF_3)_2CHOCH_2Cl$ (108 g, 0.5 mole) was mixed with $(Et)_3N\cdot 3HF$ (53 g, 0.33 mole) and $(Et)_3N$ (33 g, 0.33 mole) and heated at 60° C. with stirring for six hours. Water was added and the insoluble product (83 g) separated. This product was analyzed by gas chromatography using a 15'×⅛" 20% carbowax on chromosorb column at 125° C. The product had the following composition: 70% $(CF_3)_2CHOCH_2F$ and 30% $(CF_3)_2CHOCH_2Cl$. This represents a conversion of 58% and a yield of 75%.

Example 27

$(CF_3)_2CHOCH_2Cl$ (108 g, 0.5 mole) was mixed with $(Et)_3N\cdot 3HF$ (27 g, 0.5 mole) and $(Et)_3N$ (33 g, 0.33 mole) and heated at 60–65° C. with stirring for seven hours. The product was separated by addition of water to give 76 g. This product was analyzed by gas chromatography using a 15'×⅛" 20% carbowax on chromosorb column at 125° C. The product had the following composition: 81% $(CF_3)_2CHOCH_2F$ and 19% $(CF_3)_2CHOCH_2Cl$. This represents a conversion of 62% and a yield of 73%.

Example 28

Anhydrous hydrogen fluoride (5 g) was added to di-isopropylethyl amine (32 g) and then mixed with $(CF_3)_2CHOCH_2Cl$ (54 g). The mixture was heated at 70° C. for five hours. The product was isolated by azeotropic distillation from water to give 41 g. This product was analyzed by gas chromatography using a 15'×⅛" 20% carbowax on chromosorb column at 125° C. The product had the following composition: 70% $(CF_3)_2CHOCH_2F$ and 30% $(CF_3)_2CHOCH_2Cl$. This represents a conversion of 57% and a yield of 73%.

Example 29

$(CF_3)_2CHOCH_2Cl$ (54 g, 0.25 mole) was mixed with $(Et)_3N\cdot 3HF$ (16 g, 0.1 mole) and tributyl amine (37 g, 0.2 mole) and heated at 60–70° C. for seven hours. The product was isolated by azeotropic distillation to give 45 g of product. This product was analyzed by gas chromatography using a 15'×⅛" 20% carbowax on chromosorb column at 125° C. The product had the following composition: 65% $(CF_3)_2CHOCH_2F$ and 35% $(CF_3)_2CHOCH_2Cl$. This represents a conversion of 58% and a yield of 78%.

Example 30

$(CF_3)_2CHOCH_2Cl$ (54 g, 0.25 mole) was mixed with tributyl amine hydrofluoride (60 g, 0.29 mole) and heated at 60–70° C. for seven hours. The product was isolated by azeotropic distillation from water to give 44 g of product. This product was analyzed by gas chromatography using a 15'×⅛" 20% carbowax on chromosorb column at 125° C. The product had the following composition: 60% $(CF_3)_2CHOCH_2F$ and 40% $(CF_3)_2CHOCH_2Cl$. This represents a conversion of 52% and a yield of 75%.

Example 31

One hundred grams of a mixture of ethers prepared by chlorination of $(CF_3)_2CHOCH_3$ having the following composition: $(CF_3)_2CHOCH_3$ (8.3%), $(CF_3)_2CHOCH_2Cl$ (83%), and $(CF_3)_2CHOCHCl_2$ (8.39%) was mixed with $(Et)_3N\cdot 3HF$ (29.4 g) and $(Et)_3N$ (35.2 g) and heated at 70–75° C. for 16 hours. At the end of this time, the mixture was washed with aqueous 5% HCl to recover 76 g of product. This product was analyzed by gas chromatography using a 15'×⅛" 20% carbowax on chromosorb column at 125° C. The product contained 82% $(CF_3)_2CHOCH_2F$. This represents a yield of 73%.

The above description is provided for the purpose of describing embodiments of the invention and is not intended to limit the scope of the invention in any way. It will be apparent to those skilled in the art that various modifications and variations can be made in the method of preparation of sevoflurane without departing from the spirit or scope of the invention. Thus, it is intended that the present invention cover the modifications and variations of this invention provided they come within the scope of the appended claims and their equivalents.

What is claimed is:

1. A method for the preparation of sevoflurane which comprises:
   (a) providing a liquid mixture comprising $(CF_3)_2CHOCH_2Cl$, hydrogen fluoride, an amine, and water; and
   (b) reacting the mixture; to form $(CF_3)_2CHOCH_2F$.

2. The method of claim 1, wherein the mixture is reacted by heating.

3. The method of claim 1, wherein the mixture is reacted by heating at 40° C. to 80° C.

4. The method of claim 1, wherein the mixture is reacted by heating at 55° C. to 65° C.

5. The method of claim 1, wherein the amine is selected from a primary amine, a secondary amine, or a tertiary amine.

6. The method of claim 5, wherein the amine is selected from propylamine or diethylamine.

7. The method of claim 5, wherein the amine is a tertiary amine.

8. The method of claim 7, wherein the tertiary amine is a trialkylamine.

9. The method of claim 8, wherein the trialkylamine is selected from triethylamine, tripropylamine, triisopropylamine, tributylamine, dimethyl ethyl amine, di-isopropyl ethyl amine, or mixtures thereof.

10. The method of claim 1, wherein the amine is a cyclic amine.

11. The method of claim 10, wherein the cyclic amine is selected from pyrrolidine, N-methyl pyrrolidine, or piperidine.

12. The method of claim 1 wherein the mole ratio of the $(CF_3)_2CHOCH_2Cl$ to the hydrogen fluoride is from 1:1 to 1:2.

13. The method of claim 1, wherein the mole ratio of the $(CF_3)_2CHOCH_2Cl$ to the amine is from 1:0.3 to 1:2.

14. The method of claim 3, wherein the mixture is reacted for 4 to 12 hours.

15. The method of claim 3, wherein the mixture is reacted for 4 to 10 hours.

16. The method of claim 3, wherein the mixture is reacted for 4 to 7 hours.

17. The method of claim 1, wherein the yield of the reaction is at least 50 percent.

18. The method of claim 1, wherein the yield of the reaction is at least 65 percent.

19. The method of claim 1, wherein the yield of the reaction is at least 75 percent.

20. The method of claim 1, wherein the conversion of the reaction is at least 50 percent.

21. The method of claim 1, wherein the conversion of the reaction is at least 60 percent.

22. The method of claim 1, wherein the conversion of the reaction is at least 70 percent.

23. The method of claim 1, wherein the mixture comprises 1 to 25 percent by weight of water.

24. The method of claim 1, wherein the mixture comprises 1 to 15 percent by weight of water.

25. The method of claim 1, wherein the mixture comprises 3 to 10 percent by weight of water.

* * * * *

UNITED STATES PATENT AND TRADEMARK OFFICE
CERTIFICATE OF CORRECTION

PATENT NO. : 5,969,193
DATED : October 19, 1999
INVENTOR(S) : Ross C. Terrell

It is certified that error appears in the above-identified patent and that said Letters Patent is hereby corrected as shown below:

Column 1, line 26, replace "($CF_3CHCIOCHF_2$)" with --($CF_3CHClOCHF_2$).

Column 2, line 1, replace "1,1, 1,3,3,3-hexafluoroisopropyl" with --1,1,1,3,3,3-hexafluoroisopropyl--; line 14, replace "1,1, 1,3,3,3-hexafluoroisopropyl" with --1,1,1,3,3,3-hexafluoroisopropyl--.

Column 3, line 19, replace "1,1,1,3,3,3 hexafluoroisopropyl" with --1,1,1,3,3,3-hexafluoroisopropyl--.

Column 5, lines 18-19, replace "photochemnically" with --photochemically--; line 34, replace "sed" with --used--.

Column 6, line 17, replace "15" with --15'--.

Column 8, line 44, replace "1/8" with --1/8"--.

Column 9, line 28, delete "35"; line 41, replace "mixare" with --mixture--; line 44, replace "1/8" with --1/8"--.

Column 10, line 49, replace "3BF" with --3HF--; line 58, replace "Example 24" with --Example 25--.

Claim 1, lines 3-4, replace "($CF_3)_2CHOCH_2Cl$" with ---($CF_3)_2CHOCH_2Cl$--.

Signed and Sealed this

Ninth Day of May, 2000

Q. TODD DICKINSON

*Attest:*

*Attesting Officer*        *Director of Patents and Trademarks*